United States Patent
Vedage et al.

(10) Patent No.: US 7,399,886 B2
(45) Date of Patent: Jul. 15, 2008

(54) AMINOPROPYLATION OF ALCOHOLS IN THE PRESENCE OF AMIDE OR ETHER SOLVENTS

(76) Inventors: Garnini Ananda Vedage, 4608 Ashley La., Bethlehem, PA (US) 18017; Eugene George Lutz, 277 Mountain Rd., Lenhartsville, PA (US) 19534; Matthew J. Engel, 1049 Harris Dr., Emmaus, PA (US) 18049

( * ) Notice: Subject to any disclaimer, the term of this patent is extended or adjusted under 35 U.S.C. 154(b) by 966 days.

(21) Appl. No.: 10/655,145

(22) Filed: Sep. 4, 2003

(65) Prior Publication Data

US 2005/0054872 A1    Mar. 10, 2005

(51) Int. Cl.
*C07D 209/30*    (2006.01)
(52) U.S. Cl. .................. 564/491; 564/490; 564/491
(58) Field of Classification Search .......... 564/490, 564/491
See application file for complete search history.

(56) References Cited

U.S. PATENT DOCUMENTS

| 3,978,122 A |   | 8/1976 | Stauner et al. |
| 4,146,560 A |   | 3/1979 | Larkin et al. |
| 4,313,004 A |   | 1/1982 | Kluger et al. ............... 564/491 |
| 5,075,507 A | * | 12/1991 | Carr et al. ................... 564/491 |
| 5,869,653 A |   | 2/1999 | Johnson ..................... 540/331 |

FOREIGN PATENT DOCUMENTS

| DE | 25 55 735 | 6/1977 |
| GB | 1419213 | 12/1975 |

* cited by examiner

*Primary Examiner*—Kamal A. Saeed
*Assistant Examiner*—Janet L. Coppins

(57) ABSTRACT

This invention relates to an improved hydrogenation process for the preparation of etheramines. In the process, cyanoethylated alcohols, i.e., the reaction product of an alcohol with (meth)acrylonitrile, are contacted with hydrogen in the presence of a sponge cobalt catalyst. The improvement in the process resides in effecting the hydrogenation process utilizing a cyanoethylated alcohol feedstock contaminated with byproduct acrylonitrile and utilizing a solvent that solubilizes byproduct (meth)acrylonitrile present in the feedstock. Specific classes of solvents employed are ethers and amides.

22 Claims, No Drawings

AMINOPROPYLATION OF ALCOHOLS IN THE PRESENCE OF AMIDE OR ETHER SOLVENTS

BACKGROUND OF THE INVENTION

Cyanoethylethers are widely used as a feedstock for the production of primary amines. These cyanoethylethers are commonly produced by the reaction of acrylonitrile or methacrylonitrile with an alcohol. Diaminopropyldiethyleneglycol (DAPDEG) is a valuable diprimary amine produced by a two step process involving the cyanoethylation of diethylene glycol followed by hydrogenation of the thus formed bis(2-cyanoethyl)diethylene glycol. One of the problems encountered during the hydrogenation of cyanoethylated alcohols, and, particularly in the hydrogenation of bis(2-cyanoethyl) diethyleneglycol, is the continuous loss of catalyst activity and selectivity to the product.

The following patents and articles are representative of the art in the cyanoethylation of alcohols such as glycols.

U.S. Pat. No. 4,313,004 discloses the hydrogenation of cyanoethers in the presence of ammonia and sodium hydroxide over a nickel catalyst at elevated pressures (800-2000 psig) and temperatures of 90-160° C. It is suggested that the hydrogenation may be carried out in the presence or absence of a solvent. To minimize cleavage, the nitrile is added incrementally to the hydrogenation reactor. High yields of diamines (95-98%) are obtained.

U.S. Pat. No. 5,869,653 disloses a process for the catalytic hydrogenation of nitrites formed by the cyanoethylation of glycols or the cyanoethylation of amines in the presence of a sponge or Raney cobalt catalyst. Lithium hydroxide is added to achieve high rates of primary amine formation.

U.S. Pat. No. 5,075,507 discloses a process for the separation of unreacted acrylonitrile in a process for the cyanoethylation of glycols. In the process, a primary of secondary amine is added to the reaction medium. The process may be carried out in the presence or absence of a solvent which solvents include alcohols and hydrocarbons.

SUMMARY OF INVENTION

This invention relates to an improved hydrogenation process for the preparation of etheramines, wherein cyanoethylated alcohols, i.e., the reaction product of an alcohol with (meth)acrylonitrile, are contacted with hydrogen in the presence of a catalyst. The improvement in the process resides in effecting the hydrogenation process utilizing an ether or amide solvent that solubilizes byproduct (meth)acrylonitrile and poly(meth)acrylonitrile present in the feedstock or produced during the hydrogenation.

Significant advantages can be achieved by the use of specific types of solvents in the catalytic hydrogenation of cyanoethylated alcohols, particularly cyanoethylated ether glycols. These include:
  an ability to reduce the catalyst levels necessary to maintain reaction rate in the hydrogenation process; and,
  an ability to use the catalysts over many cycles without regenerative treatment.

DETAILED DESCRIPTION OF THE INVENTION

The cyanoethylated ethers, which constitute the basis of the feedstock for the improved hydrogenation process, are formed by the reaction of acrylonitrile or methacrylonitrile with an alcohol. In carrying out that reaction, a byproduct comprised of unreacted (meth)acrylonitrile and polymerized (meth)acrylonitrile is formed and small amounts remain after purification. It is believed that the presence of byproduct (meth)acrylonitrile is believed to be a major contributor to catalyst deactivation during conversion of the nitrile to the amine. It is also thought that some byproduct (meth)acrylonitrile, in polymerized form, is generated in the hydrogenation process and this too, contributes to catalyst deactivation. Catalyst deactivation, it is thought, is caused by byproduct and unreacted (meth)acrylonitrile being polymerized within the catalyst sites or polymerized (meth)acrylonitrile adsorbed on the surface of the catalyst.

It has been found that effecting the hydrogenation of cyanoethylated alcohols, as distinguished from cyanoethylated amines, in the presence of select solvents can improve catalyst activity and catalyst life. The improvement in the hydrogenation process resides in the use of an ether or amide solvent to overcome a substantial problem of rapid catalyst deactivation. In the past, common practice involved the use of a small amount of water, an alcohol, or a hydrocarbon as a carrier in the hydrogenation process.

Solvents to be used for the hydrogenation of cyanoethylated alcohols and the formation of aminoethylated alcohols and found to contribute to catalyst life include lower $C_{1-8}$ alkyl and cycloalkyl ethers such as tetrahydrofuran, dimethyl ether, diethyl ether, dibutyl ether and methyl-tertiary-butyl ether. Specific amides include $C_{1-8}$ alkyl amides and $C_{5-10}$ cyclic amides, such as dimethylformamide, acetamide, N-methylpyrrolidone, etc. Mixtures of solvents cited herein can also be used.

The level of ether and amide solvent employed is not critical. Functionally, there should be sufficient solvent present in the reaction medium to effect washing of the catalyst surface and removal of byproduct (meth)acrylonitrile. It should also be present in an amount to at least partially dissolve polymerized (meth)acrylonitrile on the surface of the catalyst. The major side effect of excessive levels of solvent is one of increased recovery cost. Typical solvent levels for the hydrogenation process are from 5 to 100%, preferably from 20 to 50%, by weight of the cyanoethylated alcohol to be hydrogenated.

The cyanoethylated derivatives suited as feedstocks for hydrogenation and conversion to the aminopropyl alcohol are based on the reaction of alcohols with (meth)acrylonitrile. Representative alcohols are monoalcohols, polyols, and ether derivatives thereof. Specifically, suited for forming cyanoethylated derivatives are the $C_1$-$C_{30}$ alkanols and $C_{1-8}$ alkylether alcohols, aliphatic glycols, aliphatic ether glycols and polyols. Representative $C_{1-30}$ and preferably $C_{1-8}$ alkanols include methanol, ethanol, ethanol, the propanols, the butanols, and hexanol. The $C_{1-8}$ alkylether alcohols include methoxy methanol, methoxy ethanol, ethoxy ethanol, ethoxy propanol, propoxy ethanol and propoxy propanol. Representative aliphatic glycols include the $C_{2-8}$ aliphatic glycols such as ethylene glycol, propylene glycol, butylene glycol, and pentane glycol, and the ether glycols such as diethylene glycol, and dipropylene glycol. Representative polyols include glycerin, sorbitol, and mannitol as well as polymeric polyether polyols having a number average molecular weight of up to about 4 million. Specific examples of polymeric polyols include polyethylene glycol, polypropylene glycol, polybutylene polyol and polytetrahydrofuran.

Favored cyanoethylethers produced by the cyanoethylation of such alcohols include methoxypropionitrile, ethoxypropionitrile, biscyanoethylether, bis-(2-cyanoethyl)ethylene glycol, bis-(2-cyanoethyl)diethylene glycol, mono-(2-cyanoethyl)diethylene glycol, and bis(2-cyanoethyl) tetramethylene glycol, mono and polycyanoethylated glycerin, mono and polycyanoethylated sorbitol and mono and polycyanoethylated mannitol.

The hydrogenation of the cyanoethylated alcohols can be conducted in conventional hydrogenation equipment, e.g., a stirred tank or loop reactor, a continuous stirred tank reactor, a continuous gas lift reactor, a fixed-bed plug flow reactor, a trickle-bed reactor, a bubble column reactor or a sieve-tray reactor. Preferred methods of operation include semi-batch and continuous back-mix.

The reduction of the cyanoethylated alcohol with hydrogen to the amine is generally carried out under a hydrogen pressure of from 1 to 300 bars, typically from 5 to 80 bars, and at temperatures of from about 60 to 160° C. Typical reaction times range from 15 to 600 minutes.

The catalyst used in the hydrogenation process is conventional in the art although typically the catalytic metal is sponge cobalt, or as it is sometimes called, Raney cobalt. Raney nickel, nickel, palladium, platinum, rhodium and ruthenium metals carried on a support such as alumina, silica, and the like, can also be used. Conventional promoters may be present in the catalyst in conventional amounts. Examples of promoters include Group VI and Group VIII metals such as chromium, iron, molybdenum, nickel, and so forth. Lithium hydroxide is also used as a preferred promoter.

The following examples are provided to illustrate various embodiments of the invention and are not intended to limit the scope thereof.

CONTROL EXAMPLE 1

Semi-Batch Hydrogenation of Cyanoethylated Diethylene Glycol in the Presence of Water In a one-liter batch reactor a heel was formed by adding 266 grams of water, 13.1 grams of Grace 2724 sponge cobalt catalyst to a reactor. The reactor was pressure cycled three times with nitrogen, three-times with hydrogen, and then, heated to 60° C. To this reactor was incrementally added 310 grams of nitrile feed in four hours. The nitrile feed was made by reacting diethylene glycol (DEG) (LiOH present in an amount of 1000 ppm) with acrylonitrile at a molar ratio of 1:1.3 such that equimolar concentrations of monocyanoethyl (DEG) and dicyanoethylDEG were present. Once the hydrogenation was over the product was removed using a filter, and then, the subsequent runs were started using the same catalyst with fresh solvent and feed. The subsequent hydrogenation reactions then were carried out at 800 psig (56 bar) and 60° C., semi batch. The results are shown in the Table.

CONTROL EXAMPLE 2

Semi-Batch Hydrogenation of Cyanoethylated Diethylene Glycol in the Presence of Methanol In a one-liter batch reactor a heel was formed by adding 254 grams of methanol, 8.5 grams of Grace 2724 sponge cobalt catalyst to a reactor. The reactor was pressure cycled three times with nitrogen, three-times with hydrogen, and then, heated to 120° C. To this reactor was incrementally added 423 grams of nitrile feed in five hours. The nitrile feed was made by reacting DEG (LiOH present at 1000 ppm) with acrylonitrile at a molar ratio of 1:2.03 such that the concentration of dicyanoethyl DEG and monocyanoethyl DEG in the reaction product was about 9:1. Once the hydrogenation was over the product was removed using a filter, and then, the subsequent runs were started using the same catalyst with fresh solvent and feed. The subsequent hydrogenation reactions were carried out at 800 psig (56 bar) and 120° C. The results are shown in the Table.

CONTROL EXAMPLE 3

Semi-Batch Hydrogenation of Cyanoethylated Diethylene Glycol in the Presence of Diaminopropydiethyleneglycol In a one-liter batch reactor a heel was formed by adding 302 grams of DAPDEG, 15 grams of Grace 2724 sponge cobalt catalyst. The reactor was pressure cycled three times with nitrogen and three times with hydrogen. Then, under hydrogen pressure, the contents were heated to 125° C. To this reactor was incrementally added 301 g of nitrile feed in four hours. The nitrile feed was made by reacting DEG (LiOH present at 1000 ppm) with acrylonitrile at a molar ratio of 1:2.1 such that the concentration of dicyanoethyl DEG and monocyanoethyl DEG was about 9:1 in the product. Once the hydrogenation was over the product was removed using a filter, and then, the subsequent runs were started using the same catalyst with fresh solvent and feed. The hydrogenation was carried out at 900 psig (63 bar) and 125° C. The results are shown in the Table.

EXAMPLE 4

Semi-Batch Hydrogenation of Cyanoethylated Diethylene Glycol in the Presence of Dimethylformamide In a one-liter batch reactor a heel was formed by adding 120 grams of dimethylformamide (DMF), 7.2 grams of Grace 2724 sponge cobalt catalyst. The reactor was pressure cycled three times with nitrogen and three times with hydrogen. The contents were heated to 120° C. To this reactor was incrementally added 360 grams of nitrile feed in four hours. The nitrile feed was made by reacting DEG (LiOH present at 1000 ppm) with acrylonitrile at a molar ratio of 1:2.03 such that the concentration of dicyanoethyl DEG and monocyanoethyl DEG was about 9:1 in the product. Once the hydrogenation was over the product was removed using a filter, and then, the subsequent runs were started using the same catalyst with fresh solvent and feed. The subsequent hydrogenation reactions were carried out at 800 psig (56 bar) and 120° C. The results are shown in the Table.

EXAMPLE 5

Semi-Batch Hydrogenation of Cyanoethylated Diethylene Glycol in the Presence of Methyl-Tertiary-Butylether In a one-liter batch reactor a heel was formed by adding 120 grams of methyl-tertiary-butylether (MTBE), 7.2 grams of Grace 2724 sponge cobalt catalyst. The reactor was pressure cycled three times with nitrogen and three times with hydrogen. The contents were heated to 120° C. To this reactor was incrementally added 360 grams of nitrile feed in five hours. The nitrile feed was made by reacting DEG (LiOH present at 1000 ppm) with acrylonitrile at a molar ratio of 1:2.03 such that the concentration of dicyanoethyl DEG and monocyanoethyl DEG was about 9:1 in the product. Once the hydrogenation was over the product was removed using a filter, and then, the subsequent runs were started using the same catalyst with fresh solvent and feed. The subsequent hydrogenation reactions were carried out at 800 psig (56 bar) and 120° C. The results are shown in the Table.

EXAMPLE 6

Semi-Batch Hydrogenation of Cyanoethylated Diethylene Glycol in the Presence of Tetrahydrofuran In a one-liter batch reactor a heel was formed by adding 120 grams of tetrahydrofuran (THF), 7.3 grams of Grace 2724 sponge cobalt catalyst. The reactor was pressure cycled three times with nitrogen and three times with hydrogen. The contents were heated to 120° C. To this reactor was incrementally added 360 grams of nitrile feed in four hours. The nitrile feed was made by reacting DEG (LiOH present at 1000 ppm) with acrylonitrile at a molar ratio of 1:2.03 such that the concentration of dicyanoethyl DEG and monocyanoethyl DEG was about 9:1 in the product. Once the hydrogenation was over the product was removed using a filter, and then, the subsequent runs were started using the same catalyst with fresh solvent and feed. The subsequent hydrogenation reactions were carried out at 800 psig (bar) and 120° C. The results are shown in the Table.

TABLE

| Catalyst Use # | Addition Time, hrs | Temp. ° C. | Pressure, psig | Catalyst loading, % | Heel | DEG | Mono APDEG | DAPDEG | APDAP DEG | DAPDEG SEC A | Heavies/ Others |
|---|---|---|---|---|---|---|---|---|---|---|---|
| Control Ex. 1 | | | | | | | | | | | |
| 1 | 4 | 60 | 800 | 4.2 | 46% Water | 8.60 | 39.24 | 52.12 | | | |
| 2 | 4 | 60 | 800 | 4.2 | 46% Water | 12.62 | 40.50 | 46.91 | | | |
| 3 | 4 | 60 | 800 | 4.2 | 46% Water | 19.48 | 42.20 | 38.30 | | | |
| 4 | 4 | 60 | 800 | 4.2 | 46% Water | 25.39 | 42.60 | 31.36 | | | |
| Control Ex. 2 | | | | | | | | | | | |
| 1 | 5 | 120 | 800 | 2 | 37% Methanol | | 8.1 | 89.5 | 1.1 | 1.3 | |
| 2 | 5 | 120 | 800 | 2 | 37% Methanol | | 16.4 | 72.2 | 1.5 | 9.8 | |
| 3 | 5 | 120 | 800 | 2 | 37% Methanol | | 22.2 | 32.9 | 6.9 | 15.6 | 22.2 |
| Control Ex. 3 | | | | | | | | | | | |
| 1 | 4 | 125 | 900 | 5 | 50% DAPDEG | | 11.73 | 86.23 | 2.04 | | |
| 2 | 4 | 125 | 900 | 5 | 50% DAPDEG | | 17.7 | 79.67 | 2.6 | | |
| 3 | 4 | 125 | 900 | 5 | 50% DAPDEG | | 23.5 | 72.52 | 4 | | |
| 4 | 4 | 125 | 900 | 5 | 50% DAPDEG | | 28.26 | 65.42 | 6.32 | | |
| Ex. 4 | | | | | | | | | | | |
| 1 | 5 | 120 | 800 | 2 | 25% DMF | | 7.6 | 87.3 | 0.6 | 2.8 | 1.7 |
| 2 | 5 | 120 | 800 | 2 | 25% DMF | | 7.6 | 89.5 | 0.7 | 1.5 | 0.7 |
| 3 | 5 | 120 | 800 | 2 | 25% DMF | | 8.1 | 90 | 0.4 | 0.6 | 0.9 |
| 4 | 5 | 120 | 800 | 2 | 25% DMF | | 8.7 | 89.6 | 0.4 | 0.8 | 0.5 |
| 5 | 5 | 120 | 800 | 2 | 25% DMF | | 9.2 | 88.5 | 0.5 | 0.8 | 1.0 |
| 6 | 5 | 120 | 800 | 2 | 25% DMF | | 9.4 | 88.6 | 0.5 | 0.6 | 0.9 |
| 7 | 5 | 120 | 800 | 2 | 25% DMF | | 9.4 | 88.5 | 0.4 | 0.6 | 1.1 |
| 8 | 5 | 120 | 800 | 2 | 25% DMF | | 7.4 | 90 | 0.8 | 1 | 0.8 |
| 9 | 5 | 120 | 800 | 2 | 25% DMF | | 7.9 | 90.1 | 0.5 | 0.8 | 0.7 |
| Ex. 5 | | | | | | | | | | | |
| 1 | 5 | 120 | 800 | 2 | 25% MTBE | | 9.1 | 89 | 1.1 | 0.8 | |
| 2 | 5 | 120 | 800 | 2 | 25% MTBE | | 7.3 | 92.7 | | | |
| 3 | 5 | 120 | 800 | 2 | 25% MTBE | | 7 | 93 | | | |
| 4 | 5 | 120 | 800 | 2 | 25% MTBE | | 7 | 93 | | | |
| Ex. 6 | | | | | | | | | | | |
| 1 | 5 | 120 | 800 | 2 | 25% THF | | 6.8 | 92.8 | 0.4 | | |
| 2 | 5 | 120 | 800 | 2 | 25% THF | | 6.9 | 93.1 | 0 | | |
| 3 | 5 | 120 | 800 | 2 | 25% THF | | 7 | 93 | 0 | | |

DEG—diethyleneglycol
DAPDEG—diaminopropyldiethyleneglycol
DAPDEG Sec A—DAPDEG Secondary Amine
Mono APDEG—mono aminopropyldiethylene glycol
APDAPDEG—AminopropylDAPDEG Control Example 1 shows the selectivity to the diaminopropyl diethylene glycol (DAPDEG) in the first use was 52% and by the 4$^{th}$ use the selectivity dropped to 31%, showing significant catalyst deactivation. This example shows that water is not very effective as a carrier/solvent in preventing catalyst deactivated in the hydrogenation process.

Control Example 2 shows the selectivity to DAPDEG in the first use was 89%. By the 3$^{rd}$ use, the catalyst was severely deactivated and the selectivity to DAPDEG dropped to 33%.

Control Example 3 shows the selectivity to the DAPDEG in the first use was 86% and by the 4$^{th}$ use the catalyst was severely deactivated and the selectivity DAPDEG drops to 65%. The data from Control Examples 2-3 show that similar to water, methanol, and DAPDEG are not effective as solvent/carriers in preventing catalyst deactivation.

Example 4 surprisingly shows the selectivity to DAPDEG was 87% in the first use and did not show rapid deactivation with use. Over a period of 9 uses, the selectivity did not change. These results clearly show that using DMF as a solvent is beneficial in the hydrogenation of cyanoethylalcohols to aminoethers. Also, with DMF as a solvent, it was possible to use a 2% catalyst loading compared to greater than 3% used in Control Examples 1-3 to achieve the same level of conversion.

Example 5 shows excellent results of a 2% catalyst level and excellent conversion over 4 uses.

Example 6 shows excellent results of a 2% catalyst level and excellent conversion over many uses.

In summary, the data in Table 1 show that the use of certain ethers or amide solvents can reduce the rate of catalyst deactivation in the hydrogenation of cyanoethyl ethers. For example, the results show that after 9 uses of the catalyst (Example 4) there is no loss of selectivity, compared to losses of greater than 40% selectivity in the first 3 uses of the catalyst employing the solvents of Control Examples 1-3. As a result, it is possible to use one half to one fourth of the traditional loading of the catalyst with no significant deactivation in about 10 uses. Commercially, it is desirable to obtain at least 8 uses of the catalysts prior to effecting regeneration.

The invention claimed is:

1. In a process for the hydrogenation of a cyanoethylether formed by the reaction of a reaction mixture comprised of acrylonitrile or methacrylonitrile with an alcohol in the presence of a catalyst and contaminated with unreacted byproduct (meth)acrylonitrile, the improvement in the process which comprises:
utilizing an amide or ether solvent that solubilizes said unreacted byproduct (meth)acrylonitrile or poly(meth)acrylonitrile generated during the hydrogenation.

2. The process of claim 1 wherein the solvent is selected from the group consisting of a $C_{1-8}$ alkyl ether, a $C_{5-10}$ cycloalkyl ether, a $C_{1-8}$ alkyl amide, a $C_{5-10}$ cyclic amide, and mixtures thereof.

3. The process of claim 2 wherein acrylonitrile is reacted with the alcohol.

4. The process of claim 3 wherein the solvent is selected from the group consisting of tetrahydrofuran, dimethyl ether, diethyl ether, dibutyl ether, methyl-tertiary-butyl ether, and mixtures thereof.

5. The process of claim 4 wherein the alcohol is selected from the group consisting of a $C_1$-$C_{30}$ alkanol, a $C_{1-8}$ alkylether alcohol, a polyol, and mixtures thereof.

6. The process of claim 5 wherein the alcohol is selected from the group consisting of methanol, ethanol, propanol, butanol, hexanol, methoxy methanol, methoxy ethanol, ethoxy ethanol, ethoxy propanol, propoxy ethanol, propoxy propanol, and mixtures thereof.

7. The process of claim 4 wherein the alcohol is an aliphatic glycol selected from the group consisting of a $C_{2-8}$ aliphatic glycol, a $C_{2-8}$ ether glycol, and mixtures thereof.

8. The process of claim 7 wherein the aliphatic glycol is selected from the group consisting of ethylene glycol, propylene glycol, butylene glycol, pentane glycol, diethylene glycol, and dipropylene glycol.

9. The process of claim 4 wherein the alcohol is a polyol selected from the group consisting of glycerin, sorbitol, mannitol, and a polymeric polyether polyol having a number average molecular weight of up to about 4 million.

10. The process of claim 9 wherein the polyol is a polymeric polyether polyol selected from the group consisting of polyethylene glycol, polypropylene glycol, polybutylene polyol, and polytetrahydrofuran.

11. The process of claim 4 wherein the catalyst is comprised of a cobalt metal.

12. The process of claim 11 wherein the cyanoethylether is selected from the group consisting of bis-(2-cyanoethyl)ethylene glycol, bis-(2-cyanoethyl)diethylene glycol, mono-(2-cyanoethyl)diethylene glycol, and bis(2-cyanoethyl)tetramethylene glycol.

13. The process of claim 12 wherein the cyanoethylether is bis-(2-cyanoethyl)diethylene glycol.

14. The process of claim 12 wherein the solvent is methyl-tertiary-butyl ether.

15. The process of claim 2 wherein the solvent is a $C_{1-8}$ alkyl amide or a $C_{5-8}$ cycloalkyl amide.

16. The process of claim 15 wherein the solvent is an amide selected from the group consisting of dimethylformamide, acetamide, and N-methyl pyrrolidone.

17. The process of claim 16 wherein acrylonitrile is reacted with the alcohol.

18. The process of claim 17 wherein the alcohol is selected from the group consisting of a $C_1$-$C_{30}$ alkanol, a $C_{1-8}$ alkylether alcohol, and mixtures thereof.

19. The process of claim 18 wherein the alcohol is selected from the group consisting of methanol, ethanol, propanol, butanol, and hexanol, methoxy methanol, methoxy ethanol, ethoxy ethanol, ethoxy propanol, propoxy ethanol, and propoxy propanol.

20. The process of claim 15 wherein the alcohol is an aliphatic glycol selected from the group consisting of a $C_{2-8}$ aliphatic glycol, an ether glycol, and mixtures thereof.

21. The process of claim 20 wherein the aliphatic glycol is selected form the group consisting of ethylene glycol, propylene glycol, butylene glycol, pentane glycol, diethylene glycol, and dipropylene glycol.

22. The process of claim 21 wherein the catalyst is a cobalt metal.

* * * * *